(12) United States Patent
Endo et al.

(10) Patent No.: US 7,687,649 B2
(45) Date of Patent: Mar. 30, 2010

(54) POLYGLYCEROL, POLYGLYCEROL/FATTY ACID ESTER, AND PROCESSES FOR PRODUCING THESE

(75) Inventors: Toshio Endo, Ohtake (JP); Hidetoshi Omori, Iwakuni (JP)

(73) Assignee: Daicel Chemical Industries, Ltd., Sakai-shi (JP)

( * ) Notice: Subject to any disclaimer, the term of this patent is extended or adjusted under 35 U.S.C. 154(b) by 985 days.

(21) Appl. No.: 10/536,388

(22) PCT Filed: Nov. 28, 2003

(86) PCT No.: PCT/JP03/15295

§ 371 (c)(1),
(2), (4) Date: May 19, 2006

(87) PCT Pub. No.: WO2004/048304

PCT Pub. Date: Jun. 10, 2004

(65) Prior Publication Data

US 2006/0258823 A1    Nov. 16, 2006

(30) Foreign Application Priority Data

Nov. 28, 2002   (JP)   ............. 2002-346431

(51) Int. Cl.
*C07C 57/00* (2006.01)
(52) U.S. Cl. ..................... 554/227; 525/531
(58) Field of Classification Search ............. 554/227; 525/531
See application file for complete search history.

(56) References Cited

U.S. PATENT DOCUMENTS

| | | |
|---|---|---|
| 5,041,688 A | 8/1991 | Jakobson et al. |
| 6,278,008 B1 | 8/2001 | Endo et al. |

FOREIGN PATENT DOCUMENTS

| | | | |
|---|---|---|---|
| GB | 584971 | A | 1/1947 |
| JP | 61-43627 | A | 3/1986 |
| JP | 61-140534 | A | 6/1986 |
| JP | 5-1291 | A | 1/1993 |
| JP | 5-1291 | * | 5/1993 |

(Continued)

OTHER PUBLICATIONS

Hanriot: "Derives de la Glycerine", Ann. Chim (1879), Paris, vol. 5, No. 17, pp. 62-119, XP008064176.

*Primary Examiner*—Deborah D Carr
(74) *Attorney, Agent, or Firm*—Birch, Stewart, Kolasch, Birch LLP (57) ABSTRACT

The present invention relates to a polyglycerol significantly reduced in content of a polyglycerol having a cyclic structure formed by removal of a water molecule from a polyglycerol molecule, and to a fatty acid ester of a polyglycerol having excellent surface activity. 2 mole or more of glycidol and a catalyst are successively added to 1 mole of glycerol for a reaction to obtain a polyglycerol, in which a ratio of [total polyglycerol (1)] to [total polyglycerol (2) having a cyclic structure] is [70% or more]/[30% or less] (the total of both is 100% by weight) in terms of an intensity ratio determined by liquid chromatography/mass spectrometry; and an average polymerization degree "n" is 2 or more. A reaction of a polyglycerol with a fatty acid provides the corresponding a fatty acid ester of the polyglycerol.

13 Claims, 6 Drawing Sheets

EXAMPLE 1

FOREIGN PATENT DOCUMENTS

| | | | |
|---|---|---|---|
| JP | 05052191 | * | 8/1993 |
| JP | 7-216082 A | | 8/1995 |
| JP | 7-308560 A | | 11/1995 |
| JP | 8-109153 A | | 4/1996 |
| JP | 2000 143584 | | 5/2000 |
| JP | 2000 230191 | | 8/2000 |
| JP | 2002-30144 A | | 1/2002 |

* cited by examiner

EXAMPLE 3

FIG. 4

EXAMPLE 4

COMPARATIVE EXAMPLE 4

POLYGLYCEROL, POLYGLYCEROL/FATTY ACID ESTER, AND PROCESSES FOR PRODUCING THESE

TECHNICAL FIELD

The present invention relates to a fatty acid ester of a polyglycerol having a cyclic structure in low content, to a polyglycerol having a cyclic structure in low content used as a raw material for the fatty acid ester of a polyglycerol, and to processes for producing the same. The fatty acid ester of a polyglycerol having a cyclic structure in low content obtained by the present invention has high surface activity because of low content of a dehydrated cyclic structure, and it can be used as a food additive or a cosmetic, medical, or industrial surfactant for the purpose of emulsification, solubilization, dispersion, washing, anticorrosion, lubrication, static protection, wetting, and so on. Moreover, the polyglycerol itself can be used as humectants, thickeners, plasticizers, and for hydrophilic treatment, and so on.

BACKGROUND ART

Examples of various compounds, conventionally known as emulsifiers or solubilizers include: ethylene oxide-based nonionic surfactants such as a polyoxyethylene alkyl ether, a polyoxyethylene polyhydric alcohol/fatty acid ester, and a polyoxyethylene alkyl phenyl ether; and food surfactants such as a sorbitan/fatty acid ester, a sucrose/fatty acid ester, and a fatty acid ester of a polyglycerol (including a polyglycerol ester of interesterified ricinoleic acid).

Of those, the fatty acid ester of a polyglycerol is one of the most useful surfactants because the fatty acid ester of a polyglycerol ensures safety to a human body and to the environment, can have diverse compositions, and has high versatility. The fatty acid ester of a polyglycerol is produced by polymerizing glycerol as one of raw materials at high temperatures in the presence of an alkali catalyst such as caustic soda, deodorizing and decolorizing the resultant to obtain a polyglycerol reaction product, and subjecting the polyglycerol reaction product and a fatty acid as raw materials to an esterification reaction.

Meanwhile, known processes for industrial production of a polyglycerol used as a raw material are as follows:

(i) a process for producing a polyglycerol through recovery from a distillation residue of glycerol;

(ii) a process for producing a polyglycerol through dehydration condensation of glycerol;

(iii) a process for producing a polyglycerol through direct polymerization of epichlorohydrin, hydrolysis, and then dechlorination; and (iv) a process for producing a polyglycerol through addition of glycidol to glycerol or a polyglycerol in the presence of an alkali catalyst such as NaOH or amines, or an acidic catalyst such as acetic acid.

However, analysis of a composition distribution of the polyglycerol reaction product obtained through each of the above processes by liquid chromatography/mass spectrometry as described below confirms that produced through intramolecular dehydration are not only cyclic low molecular compounds but also a polyglycerol having a cyclic structure in considerably high content with a molecular weight ranging from several hundreds to several thousands, which are formed through removal of one to several water molecule(s) from a polyglycerol molecule.

The inventors of the present invention have found that a polyglycerol containing the above-described polyglycerol having a cyclic structure in high content has inhibited properties in hydrophilicity and the like. The inventors of the present invention have also found that deterioration of properties such as water solubility, surface activity, and the like is caused in a fatty acid ester of a polyglycerol obtained from the above-described polyglycerol and a fatty acid ester.

As a polyglycerol produced through a reaction, a reaction product obtained by reacting glycerol with epichlorohydrin or glycidol, or by reacting glycerol or a polyglycerol with epichlorohydrin, monochlorohydrin, dichlorohydrin, or glycidol has been heretofore used as it is or used after having been optionally purified.

Example of a purification process include: purification by heating under reduced pressure of several Torr in a stream of a gas such as nitrogen or water vapor for deodorization or removal of unreacted raw materials; purification by removing ionic components such as a catalyst used with an ion-exchange resin, an ion-exchange membrane, or the like; purification by removing color components or odor components using an absorbent such as active carbon; and purification by reduction treatment through hydrogenation or the like.

However, in the purification processes for a polyglycerol reaction product, the composition distribution of the resulting a polyglycerol reaction product has not been discussed in detail. Regarding a polyglycerol reaction product obtained by polymerizing the most generally used glycerol at high temperatures in the presence of an alkali catalyst such as caustic soda, and deodorizing and decolorizing the resultant, cyclic compounds having a low molecular weight such as cyclic diglycerol have been discussed extensively. However, actually, analysis on the composition distribution of a polyglycerol having a molecular weight in the range of several hundreds to several thousands has been hardly discussed in spite of a fact that a dehydration reaction is known to take place in a polyglycerol molecule.

Commercially distributed a polyglycerol is called tetraglycerol, hexaglycerol, or decaglycerol according to an average polymerization degree calculated from a hydroxyl value. However, in fact, the polyglycerol is a mixture of various glycerol polymers each having a polymerization degree from 2 to 10 or more, and may include unreacted glycerol (polymerization degree of 1).

It has been revealed that a polyglycerol of a relatively low molecular weight such as glycerol, diglycerol, or triglycerol may exist in high content in a polyglycerol containing such a mixture of various glycerols in order to adjust the average polymerization degree calculated from hydroxyl values to the same value.

JP-B 5-1291 (claim 1, lines 12-22 in the 3rd column, and Examples) discloses slightly colored polyglycerol having a large polymerization degree obtained by: adding a phosphoric acid catalyst to glycerol or a polyglycerol; and subjecting the resultant to an addition reaction with glycidol at 115 to 125° C.

JP-A7-216082 (claim 1, paragraph 0008, and Examples) discloses a process for producing a polyglycerol in which glycerol is polycondensed in a boiling state of a reaction mixture at 200 to 270° C. in the presence of an alkali.

JP-A 2002-30144 (claim 1, and Examples 1 to 12) discloses a process for producing a polyglycerol in which glycidol alone is added and allowed to react in the presence of an alkali metal halide without the use of glycerol as an initiator.

Regarding a fatty acid ester of a polyglycerol, JP-A 7-308560 [claim 1 and Comparative Example 1 (Production of a polyglycerol used in each Example)] discloses a process in which a polyglycerol obtained by distilling off low molecular weight polymers from a polyglycerol produced through polycondensation of glycerol at 240° C. in the presence of sodium hydroxide is allowed to react with a fatty acid.

Alternatively, JP-A8-109153 (claim 1 and Examples) discloses a process for producing a fatty acid ester of a polyglycerol obtained through an addition polymerization reaction of glycidol with a fatty acid. However, a product obtained through this process is restricted to a polyglycerol/mono-fatty acid ester alone.

DISCLOSURE OF THE INVENTION

An object of the present invention is to provide: a polyglycerol significantly reduced in content of a polyglycerol having a cyclic structure formed through removal of a water molecule from a polyglycerol molecule and a production process thereof; and a fatty acid ester of a polyglycerol having excellent surface activity and a production process thereof.

A polyglycerol has not been thoroughly studied so far because a polyglycerol has physical properties of high viscosity and high boiling point and thus because of difficulties in handling. In particular, significance of the presence of a polyglycerol having a cyclic structure in a polyglycerol reaction product and significance of its removal have not been recognized. However, the inventors of the present invention have realized that reduction in content of a polyglycerol having a cyclic structure is necessary. Thus, the inventors of the present invention have devoted themselves to extensive studies and have found that glycidol and a catalyst are added dropwise for a reaction with glycerol as a starting material, to thereby give a polyglycerol having a cyclic structure in low content. Thus, the inventors of the present invention have completed the present invention.

That is, a first aspect of the present invention provides a polyglycerol having a cyclic structure in low content, in which a ratio of total polyglycerol (1) represented by the following general formula [1] to total polyglycerol (2) having a cyclic structure that contains at least one cyclic structure in a molecule, that is, [the total polyglycerol (1)]:[the total polyglycerol (2) having a cyclic structure] is [70% or more]:[30% or less](the total of both is 100% by weight) in terms of an intensity ratio determined by liquid chromatography/mass spectrometry; and an average polymerization degree (repeating unit of a glycerol residue) "n" is 2 or more:

(in the formula [1], "p" represents a repeating portion of a glycerol residue and is an integer of 0 or more; and the polyglycerol molecule has a polymerization degree of "p+2").

A second aspect of the present invention provides a polyglycerol having a cyclic structure in low content according to the first aspect of the present invention, in which the polyglycerol (2) having a cyclic structure is a polyglycerol having a cyclic structure that contains a structure represented by the following general formula [2]:

(in the formula [2], "p" represents a repeating portion of a glycerol residue and is an integer of 0 or more; "q" represents a cyclic structure portion and is an integer of 1 or more; the polyglycerol molecule has a polymerization degree of "p+2q+1"; the cyclic structure portion(s) may be inserted randomly or continuously between the glycerol residues; and the polyglycerol having a cyclic structure in low content, which is a mixture of the polyglycerol molecules, has an average polymerization degree "n" of 2 or more).

A third aspect of the present invention provides a polyglycerol having a cyclic structure in low content according to the first aspect of the present invention, in which the polyglycerol (2) having a cyclic structure is a polyglycerol having a cyclic structure containing a structure represented by the following general formula [3]:

(in the formula [3], "p" represents a repeating portion of a glycerol residue and is an integer of 0 or more; and the polyglycerol molecule has a polymerization degree of "p+3").

A fourth aspect of the present invention provides a polyglycerol having a cyclic structure in low content according to the first aspect of the present invention, in which an average polymerization degree "n" is 3 to 60.

A fifth aspect of the present invention provides a polyglycerol having a cyclic structure in low content according to the first aspect of the present invention, in which: a ratio of [the total polyglycerol (1)]:[the total polyglycerol (2) having a cyclic structure] is [80% or more]:[20% or less] (the total of both is 100% by weight); and an average polymerization degree "n" is 2 to 10.

A sixth aspect of the present invention provides a polyglycerol having a cyclic structure in low content according to the first aspect of the present invention, in which a ratio of [the total polyglycerol (1)]:[the total polyglycerol (2) having a cyclic structure] is [70% or more]:[30% or less] (the total of both is 100% by weight); and an average polymerization degree "n" is greater than 10.

A seventh aspect of the present invention provides a polyglycerol having a cyclic structure in low content according to any one of the first to sixth aspects of the present invention, in which: a ratio of a component with a polymerization degree "n−1" to a polyglycerol showing the highest distribution rate (polymerization degree "n") in terms of an intensity ratio distribution determined by liquid chromatography/mass spectrometry, that is, (component with a polymerization degree "n−1")/(component with a polymerization degree "n") is 0.4 or more.

An eighth aspect of the present invention provides a process for producing a polyglycerol having a cyclic structure in low content according to the first aspect of the present invention, characterized by including successively adding 2 mole or more of glycidol and a catalyst to 1 mole of glycerol for a reaction.

An ninth aspect of the present invention provides a process for producing a polyglycerol having a cyclic structure in low content according to the eighth aspect of the present invention, in which the catalyst is a phosphoric acid-based acidic catalyst.

A tenth aspect of the present invention provides a process for producing a polyglycerol having a cyclic structure in low content according to the ninth aspect of the present invention, in which the phosphoric acid-based acidic catalyst is phosphoric acid or acidic phosphate.

A eleventh aspect of the present invention provides a process for producing a polyglycerol having a cyclic structure in low content according to any one of the eighth to tenth aspects of the present invention, in which a reaction temperature is in a range of 80 to 130° C.

A twelfth aspect of the present invention provides a polyglycerol having a cyclic structure in low content obtained through the process for producing a polyglycerol having a cyclic structure in low content according to any one of the eighth to tenth aspects of the present invention, in which a fluctuation trend of ratio of (component with a polymerization degree "n−1")/(component with a polymerization degree "n") and of (component with a polymerization degree "n+1")/(component with a polymerization degree "n") in terms of intensity ratio determined by liquid chromatography/mass spectrometry corresponds to a distribution obtained through a successive reaction of glycidol using glycerol as an initiator.

A thirteenth aspect of the present invention provides a polyglycerol having a cyclic structure in low content obtained through the process for producing a polyglycerol having a cyclic structure in low content according to the eleventh aspect of the present invention, in which a fluctuation trend of ratio of (component with a polymerization degree "n−1")/(component with a polymerization degree "n") and of (component with a polymerization degree "n+1")/(component with a polymerization degree "n") in terms of intensity ratio determined by liquid chromatography/mass spectrometry corresponds to a distribution obtained through a successive reaction of glycidol using glycerol as an initiator.

A fourteenth aspect of the present invention provides a fatty acid ester of a polyglycerol having a cyclic structure in low content, including an ester structure formed through a dehydration reaction of a polyglycerol having a cyclic structure in low content according to any one of the first to sixth aspects of the present invention with a fatty acid having 2 to 30 carbons.

A fifteenth aspect of the present invention provides a fatty acid ester of a polyglycerol having a cyclic structure in low content, including an ester structure formed through a dehydration reaction of a polyglycerol having a cyclic structure in low content according to the seventh aspect of the present invention with a fatty acid having 2 to 30 carbons.

A sixteenth aspect of the present invention provides a fatty acid ester of a polyglycerol having a cyclic structure in low content, including an ester structure formed through a dehydration reaction of a polyglycerol having a cyclic structure in low content according to the twelfth aspect of the present invention with a fatty acid having 2 to 30 carbons.

A seventeenth aspect of the present invention provides a fatty acid ester of a polyglycerol having a cyclic structure in low content, including an ester structure formed through a dehydration reaction of a polyglycerol having a cyclic structure in low content according to the thirteenth aspect of the present invention with a fatty acid having 2 to 30 carbons.

A eighteenth aspect of the present invention provides a process for producing a fatty acid ester of a polyglycerol having a cyclic structure in low content, including carrying out a dehydration reaction of a polyglycerol having a cyclic structure in low content according to any one of the first to sixth aspects of the present invention with a fatty acid having 2 to 30 carbons.

A nineteenth aspect of the present invention provides a process for producing a fatty acid ester of a polyglycerol having a cyclic structure in low content, including carrying out a dehydration reaction of a polyglycerol having a cyclic structure in low content according to the seventh aspect of the present invention with a fatty acid having 2 to 30 carbons.

A twentieth aspect of the present invention provides a process for producing a fatty acid ester of a polyglycerol having a cyclic structure in low content, including carrying out a dehydration reaction of a polyglycerol having a cyclic structure in low content according to the twelfth aspect of the present invention with a fatty acid having 2 to 30 carbons.

A twenty-first aspect of the present invention provides a process for producing a fatty acid ester of a polyglycerol having a cyclic structure in low content, including carrying out a dehydration reaction of a polyglycerol having a cyclic structure in low content according to the thirteenth aspect of the present invention with a fatty acid having 2 to 30 carbons.

BRIEF DESCRIPTION OF THE DRAWINGS

FIG. 8($a$) is a liquid chromatogram of a reaction product according to Example 3.

FIG. 8($b$) is a liquid chromatogram of a reaction product according to Comparative Example 1.

FIG. 8($c$) is a liquid chromatogram of a reaction product according to Comparative Example 2.

BEST MODE FOR CARRYING OUT THE INVENTION

Hereinafter, the present invention will be described in detail.

I. A Polyglycerol Having a Cyclic Structure in Low Content

A polyglycerol having a cyclic structure in low content of the present invention is composed of a polyglycerol (1) represented by the general formula [1] and a polyglycerol (2) having a cyclic structure containing at least one cyclic structure in a polyglycerol molecule.

[1]

In the formula [1], "p" represents a repeating portion of a glycerol residue and is an integer of 0 or more, and the polyglycerol molecule has a polymerization degree of "p+2". Thus, the formula [1] represents diglycerol having a polymerization degree of 2 if "p" is 0, triglycerol having a polymerization degree of 3 if "p" is 1, or tetraglycerol having a polymerization degree of 4 if "p" is 2, for example.

The cyclic structure portion in the polyglycerol (2) having a cyclic structure is formed through a dehydration reaction of any two hydroxyl groups of a glycerol residue in the polyglycerol (1). The cyclic structure can include various structures depending on reaction conditions and so on, and is therefore not particularly limited. Examples of a cyclic structure formed under general reaction conditions include a 1,4-dioxane structure (6-membered ring), a 1,4-dioxepane structure (7-membered ring), and a 1,5-dioxocane structure (8-membered ring).

For example, in a polyglycerol having a cyclic structure represented by the following formula [2], "p" represents a repeating portion of a glycerol residue and is an integer of 0 or more. The "q" represents a cyclic structure portion and is an integer of 1 or more. The polyglycerol molecule has a polymerization degree of "p+2q+1". The cyclic structure portion (s) may be inserted between the glycerol residues randomly or continuously, into a chain, or at a terminal. Thus, the formula [2] is composed of 1 unit of dehydrated cyclic diglycerol and 1 unit of glycerol if "p" is 0 and "q" is 1, or 2 units of glycerol and 1 unit of dehydrated cyclic diglycerol if "p" island "q" is 1, for example. Further, the formula [2] is composed of 3 units of glycerol and 1 unit of dehydrated cyclic diglycerol if "p" is 2 and "q" is 1, or 4 units of glycerol and 2 units of dehydrated cyclic diglycerol if "p" is 3 and "q" is 2, for example.

[2]

A polyglycerol having a cyclic structure in low content of the present invention is characterized in that a ratio of [total polyglycerol (1)]:[total polyglycerol (2) having a cyclic structure containing at least one cyclic structure, preferably one or two of cyclic structure(s) in the polyglycerol molecule] is [70% or more]:[30% or less] (the total of both is 100% by weight), preferably [80% or more]:[20% or less] by liquid chromatography/mass spectrometry (abbreviated as LC/MS) described below.

In a polyglycerol having a cyclic structure in low content of the present invention, the total polyglycerol having one cyclic structure is 30% or less, preferably 20% or less with respect to the total polyglycerol (1). The total polyglycerol having two cyclic structures is one third or less of the total polyglycerol having one cyclic structure, and the total polyglycerol having three cyclic structures is one fifth or less of the total polyglycerol having two cyclic structures. Thus, the polyglycerol having three cyclic structures, if any, is present in the polyglycerol in very low content.

The polyglycerol (1) in the polyglycerol having a cyclic structure in low content of the present invention has an average polymerization degree (repeating unit of a glycerol residue) "n" of 2 or more, preferably 3 to 60, particularly preferably 3 to 50.

In the polyglycerol having a cyclic structure in low content of the present invention, the ratio of a polyglycerol (2) having a cyclic structure tends to increase gradually with increasing average polymerization degree "n" of a polyglycerol (1). If the average polymerization degree "n" of a polyglycerol (1) is from 2 to 10, the ratio of [the total polyglycerol (1)]:[the total polyglycerol (2) having a cyclic structure] is [80% or more]:[20% or less], preferably [85% or more]:[15% or less], more preferably [90% or more]:[10% or less]. If the average polymerization degree "n" of a polyglycerol (1) is greater than 10, the ratio of [the total polyglycerol (1)]:[the total polyglycerol (2) having a cyclic structure] is [70% or more]:[30% or less], preferably [75% or more]:[25% or less], more preferably [80% or more]:[20% or less].

Moreover, in a polyglycerol having a cyclic structure in low content of the present invention, the ratio of a component with a polymerization degree "n−1" to a polyglycerol showing the highest distribution rate (polymerization degree "n") in terms of an intensity ratio distribution determined by liquid chromatography/mass spectrometry, that is, (component with a polymerization degree "n−1")/(component with a polymerization degree "n") is 0.4 or more, and 0.5 or more and even 0.7 or more with increasing average polymerization degree "n" of a polyglycerol (1).

Furthermore, in a polyglycerol having a cyclic structure in small amount obtained through a production process of the present invention, a fluctuation trend of ratio of (component with a polymerization degree "n−1")/(component with a polymerization degree "n") and of (component with a polymerization degree "n+1")/(component with a polymerization degree "n") in terms of intensity ratio determined by liquid chromatography/mass spectrometry corresponds to a distribution obtained through a successive reaction of glycidol using glycerol as an initiator. A polyglycerol having such a distribution easily improves solvency and acquires required HLB (hydrophilicity-lipophilicity balance).

A polyglycerol (1) may contain a low content of a branched structure having glycidol added to a secondary hydroxyl group.

A reaction product contains approximately 1 to 15%, preferably 10% or less of other compounds (e.g., a polyglycerol having a double bond in the polyglycerol molecule) in addition to the above-described polyglycerol (1) and a polyglycerol (2), and glycerol as a raw material. The content of other compounds increases with increasing average polymerization degree of a polyglycerol (1).

An LC/MS analysis system is composed of LC and MS portions, and an interface connecting them. The MS portion as a detection system operates on a principle common with that of a GC/MS analysis system, which employs a technique of detecting and identifying ionized target substances on the basis of a mass number/charge (m/z) ratio.

Processes for obtaining information from MS connected to chromatography include a mass chromatogram showing a time distribution of an intensity of an arbitrary m/z, a mass spectrum showing a relative intensity distribution of each m/z at an arbitrary time, and a total ion chromatogram (TIC) showing a time change of total intensity, not of an intensity of individual m/z, obtained by adding intensities (quantities of electricity) of all ions. Of those processes, the total ion chromatogram is preferably used.

Processes for obtaining the mass chromatogram include a scanning method for extracting a time distribution of required m/z intensity from intensity information in a time axis direction obtained through magnetic field scanning within a certain m/z range at a constant time interval, and a selected ion monitoring (SIM) method with high sensitivity for selectively detecting only an intensity of a target single m/z or intensities of a plurality of m/z's.

Examples of a basic principle of a mass spectrometer in practical use include a magnetic sector type, a quadrupole type, an ion trap type, a flying time, and a Fourier transform type. Of those spectrometers, the ion trap type spectrometer is preferred.

A polyglycerol having a cyclic structure in low content of the present invention is obtained by successively adding a catalyst and glycidol to a reactor charged with water or glycerol as an initiator for an addition polymerization reaction.

The catalyst is preferably a phosphoric acid-based acidic catalyst. Examples of the above-described phosphoric acid-based acidic catalyst include phosphoric acids and phosphates. Specific examples thereof include: phosphoric acids such as phosphoric acid, phosphoric anhydride, polyphosphoric acid, orthophosphoric acid, metaphosphoric acid, pyrophosphoric acid, triphosphoric acid, and tetraphosphoric acid; and acidic phosphates such as methyl acid phosphate, ethyl acid phosphate, isopropyl acid phosphate, butyl acid phosphate, and 2-ethylhexyl acid phosphate. It is noted that those acidic phosphates can be used in any forms such as a monoester, a diester, and a mixture thereof. Of those, phosphoric acid and acidic phosphate are preferably used. One of the above-described catalysts may be used alone, or two or more of them may be used as a mixture.

An addition amount of the catalyst is 0.001 to 1% by weight, preferably 0.01 to 0.5% by weight with respect to a resulting polyglycerol. The addition amount of less than 0.001% by weight provides a small reaction rate. On the other hand, the addition amount of more than 1% by weight easily promotes hydrolysis in esterification with a fatty acid due to the remaining phosphoric acid. As a result, the addition amount of more than 1% by weight causes a deleterious effect on the performance of a product such as insufficient stability of an aqueous solution.

Glycerol is placed in a reactor and 2 mole or more of glycidol and a catalyst are successively added to 1 mole of the glycerol for a reaction, to name one example of a reaction process.

Alternatively, in the case of using water as an initiator, water is placed in a reactor and a reaction is carried out in the same manner as that described above.

The catalyst and glycidol may be separately added dropwise (separately charged), or may be added dropwise in a mixed state. It is not preferred that the dropping of the catalyst be terminated too early compared with that of glycidol. Although the rate of dropping thereof is not particularly limited, it is preferred that the catalyst and glycidol be added dropwise at a uniform rate as a whole.

A reaction temperature is in the range of 80° C. to 130° C., preferably 85° C. to 125° C., more preferably 90° C. to 120° C. When the temperature is lower than 80° C., the reaction rate is small. When the temperature is higher than 130° C., intramolecular dehydration takes place easily, thereby increasing the content of a polyglycerol having a cyclic structure.

Moreover, the reaction is desirably carried out under an inert gas atmosphere such as nitrogen gas, and may be optionally carried out under compressed or reduced pressure conditions. The reaction rate can be increased in a reaction under compressed conditions.

A conversion of glycidol is 98% or more, preferably 99.5% or more, more preferably 99.9% or more.

The obtained polyglycerol having a cyclic structure in low content may be purified as required for use of a product. A purification process is not particularly limited, and any of processes known in the art may be employed. For example, a polyglycerol may be purified through an absorption treatment with active carbon, activated clay, or the like, a treatment under reduced pressure using water vapor, nitrogen, or the like as a carrier gas, washing with an acid or an alkali, or molecular distillation. Alternatively, unreacted polyglycerol and the like may be separated and removed through liquid-liquid distribution, or using an absorbent, a resin, a molecular sieve, a loose reverse osmosis membrane, an ultrafiltration membrane, or the like.

Furthermore, low molecular weight substances such as unreacted glycerol and glycerol dimer in the above-described reaction product may be optionally removed through distillation or the like from a polyglycerol having a cyclic structure in low content of the present invention.

II. Fatty Acid Ester of a Polyglycerol Having a Cyclic Structure in Low Content

A fatty acid ester of a polyglycerol having a cyclic structure in low content according to the present invention is a fatty acid ester of a polyglycerol having a cyclic structure in low content, which has an ester structure formed through dehydration of the above-described polyglycerol having a cyclic structure in low content of the present invention and a fatty acid.

Examples of a process for producing the fatty acid ester of a polyglycerol having a cyclic structure in low content according to the present invention can include a process through dehydration esterification of a polyglycerol having a cyclic structure in low content with a fatty acid, a process through removal of low molecular weight alcohol from an ester of a fatty acid with a low molecular weight alcohol and a polyglycerol having a cyclic structure in low content, a process through removal of a low molecular weight fatty acid from an ester of a low molecular weight fatty acid with a polyglycerol having a cyclic structure in low content and a higher fatty acid, and a process through removal of an alkali halide from a fatty acid halide, a polyglycerol having a cyclic structure in low content, and caustic alkali. Of those processes, there is economical the process through dehydration esterification of a polyglycerol having a cyclic structure in low content with a fatty acid.

In the process through dehydration esterification, for example, the dehydration esterification can be carried out under normal pressure or reduced pressure in the presence of an alkali catalyst or an acid catalyst, or in the absence of a catalyst. A polyglycerol having a cyclic structure in low content and a fatty acid must be added in an amount appropriately selected according to the purpose of a product. For example, in the case of intending to obtain a hydrophilic surfactant, a polyglycerol having a cyclic structure in low content and a fatty acid may be added in equimolar amounts by calculating weights thereof from a hydroxyl value (also referred to as an OH value) of a polyglycerol having a cyclic structure in low content and a molecular weight of a fatty acid. In the case of intending to obtain a lipophilic surfactant, mole number of the fatty acid may be increased.

The obtained fatty acid ester of a polyglycerol having a cyclic structure in low content may be purified as required for use of a product. The purification process is not particularly limited, and any of processes known in the art may be employed. For example, the fatty acid ester of a polyglycerol may be purified through an absorption treatment with activated carbon, activated clay, or the like, a treatment under reduced pressure using water vapor, nitrogen, or the like as a carrier gas, washing with an acid or an alkali or molecular distillation. Alternatively, unreacted polyglycerol and the like may be separated and removed through liquid-liquid distribution, or using an absorbent, a resin, a molecular sieve, a loose reverse osmosis membrane, an ultrafiltration membrane, or the like.

Additive

An additive may be added to the fatty acid ester of a polyglycerol having a cyclic structure in low content of the present invention to allow easy handling of a product. Examples of the additive include ethanol, propylene glycol, glycerol, a polyglycerol, water, liquid sugar, and oils and fats for reducing a viscosity of a product. One additive or two or more additives may be added to dissolve or emulsify the fatty acid ester of a polyglycerol. Alternatively, polysaccharide such as lactose or dextrin, or a protein such as caseinate may be added to pulverize the fatty acid ester of a polyglycerol.

Depending on the purpose for use, the fatty acid ester of a polyglycerol having a cyclic structure in low content of the present invention may be mixed with other surfactants as additives to produce a product of a surfactant. Examples of the other surfactants that can be used include nonionic surfactants, amphoteric surfactants, anionic surfactants, and cationic surfactants. Examples of the nonionic surfactants include: lecithin such as soybean lecithin, yolk lecithin, or rapeseed lecithin, or a partial hydrolysate thereof; monoglycerides such as monoglycerides of caprylic acid, capric acid, lauric acid, myristic acid, palmitic acid, stearic acid, behenic acid, oleic acid, elaidic acid, ricinoleic acid, and interesterified ricinoleic acid, a monoglyceride mixture thereof, or a monoglyceride of an organic acid which is an organic acid ester of the monoglyceride with an organic acid such as acetic acid, citric acid, succinic acid, malic acid, and tartaric acid; a fatty acid ester of sorbitan such as a sorbitan ester of caprylic acid, capric acid, lauric acid, myristic acid, palmitic acid, stearic acid, behenic acid, oleic acid, elaidic acid, ricinoleic acid, and interesterified ricinoleic acid; propylene glycol/ fatty acid esters such as propylene glycols of caprylic acid, capric acid, lauric acid, myristic acid, palmitic acid, stearic acid, behenic acid, oleic acid, elaidic acid, ricinoleic acid, and interesterified ricinoleic acid; and sucrose/fatty acid esters such as sucrose esters of caprylic acid, capric acid, lauric acid, myristic acid, palmitic acid, stearic acid, behenic acid, oleic acid, elaidic acid, ricinoleic acid, and interesterified riciholeic acid.

EXAMPLES

Hereinafter, the present invention will be more specifically described with reference to examples, but the present invention is not limited thereto.

It is to be noted that throughout Examples and Comparative Examples, analysis conditions for LC/MS (Liquid Chromatography/Mass Spectrometry) are as follows.

(Conditions for LC Separation)
Column: TSKgel α-2500 (7.8×300 mm) (aqueous polymeric gel column)
Temperature: 40° C.
Eluent: water/acetonitrile=7/3
Flow rate: 0.8 ml/min
Injection volume: 10 μl (sample concentration of 100 ppm)
Analysis time: 20 minutes (Conditions for MS Analysis)
Apparatus: LCQ (manufactured by ThermoQuest, ion trap type)
Ionization mode: APCI (Atmospheric Pressure Chemical Ionization), negative
Measurement range: m/z=90 to 2,000
Method for intensity ratio measurement: through a mass spectrometric analysis indicating a relative intensity distribution of each m/z at an arbitrary time.

Example 1

Figure 1:
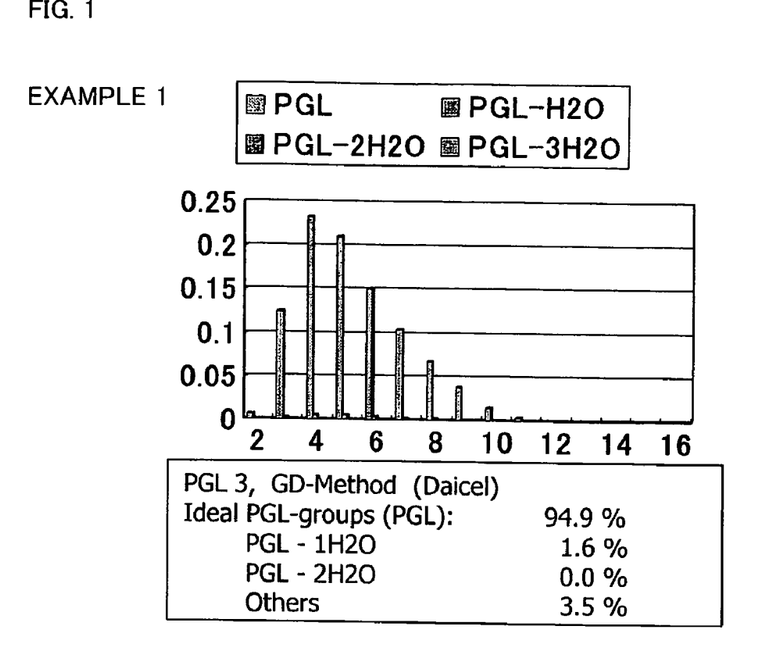
FIG. 1 is a chart showing a composition distribution of a reaction product according to Example 1.

Into a 1 L four-neck flask equipped with a nitrogen introduction pipe, a stirrer, a cooling pipe, a thermoregulator, and a dropping cylinder, 4.0 mole (368.4 g) of glycerol was added, and the glycerol was heated to 100° C. While a reaction temperature was maintained at 100° C., 8.0 mole (592.6 g) of glycidol and 1.922 g of phosphoric acid (a product of 85%) were separately dropped therein over 6 hours to continue a reaction until a concentration of oxirane in the system reached less than 0.1%. After cooling, a reaction product was taken out to obtain approximately 950 g of a polyglycerol (PGL 3: average polymerization degree of approximately 3). The polyglycerol showed an OH value of 1,170 mg-KOH/g. The obtained polyglycerol was analyzed by the above LC/MS. FIG. 1 shows the results of componential analysis. In each of figures below showing the results of componential analysis, the numbers of a horizontal axis represent degrees of polymerization of a polyglycerol, and a vertical axis indicates a relative intensity with a bar graph. On the horizontal axis, a polyglycerol (1), a polyglycerol (2) having one cyclic structure that contains one cyclic structure, and a polyglycerol (2) having a cyclic structure that contains two cyclic structures are indicated with the bar graphs drawn side by side for each polymerization degree. In each of the figures, Ideal PGL Groups (PGL) represents a polyglycerol (1), and PGL-$H_2O$, PGL-$2H_2O$, and the like, represent a polyglycerol having a cyclic structure formed through removal of one water molecule, a polyglycerol having a cyclic structure formed through removal of two water molecules, and the like, respectively.

In the intensity ratio distribution of a polyglycerol of FIG. 1, the polymerization degree "n" of a polyglycerol showing the mode (the highest distribution rate) was 4, and the ratio of (component with a polymerization degree "n−1")/(component with a polymerization degree "n") was 0.5327.

TABLE 1

Intensity ratio in componential analysis of a polyglycerol in Example 1

| | Intensity ratio in componential analysis | Ratio with respect to mode |
|---|---|---|
| Polymerization degree "n − 1" | 0.1237 | 0.5327 |
| Polymerization degree "n" | 0.2322 | 1.0000 |
| Polymerization degree "n + 1" | 0.2102 | 0.9052 |

[The polymerization degree "n" of a polyglycerol showing the highest distribution rate (mode) was 4]

As Table 1 shows, in the reaction product obtained in the polymerization step according to the process of the present invention, components with varying degrees of polymerization except unreacted glycerol provided a distribution corresponding to that obtained through a successive reaction of glycidol using glycerol as an initiator. The reaction product having such a distribution can have improved solvency and so on, though depending on kinds of solutes.

Example 2

Figure 2:
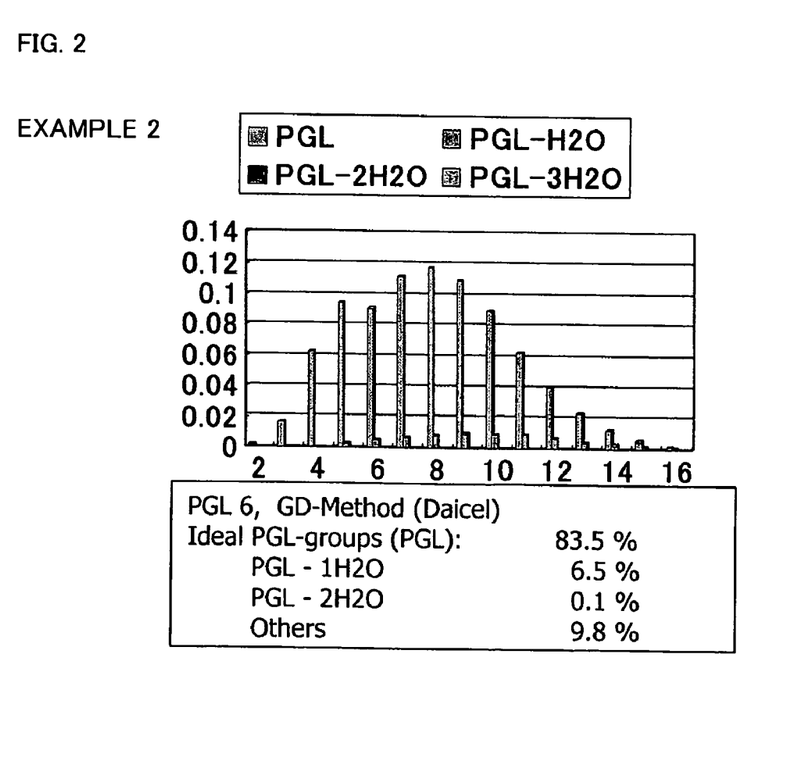
FIG. 2 is a chart showing a composition distribution of a reaction product according to Example 2.

Into a 2 liter four-neck flask having equipment similar to those of Example 1, 4.4 mole (405.2 g) of glycerol was added, and the glycerol was heated to 120° C. Subsequently, while a reaction temperature was maintained at 120° C., 22.0 mole (1,629.8 g) of glycidol and 2.035 g of phosphoric acid (a product of 85%) were separately dropped therein over 6 hours to continue the reaction until the concentration of oxirane in the system reached less than 0.1%. After cooling, a reaction product was taken out to obtain approximately 2,000 g of a polyglycerol (PGL 6: average polymerization degree of approximately 6). The polyglycerol showed an OH value of 970 mg-KOH/g. FIG. 2 shows the LC/MS analysis results of the obtained polyglycerol. As Table 2 shows, in the reaction product obtained in the polymerization step according to the process of the present invention, components with varying degrees of polymerization except unreacted glycerol provided a preferred distribution as that in Example 1.

TABLE 2

Intensity ratio in componential analysis of a polyglycerol in Example 2

| | Intensity ratio in componential analysis | Ratio with respect to mode |
|---|---|---|
| Polymerization degree "n − 1" | 0.1110 | 0.9503 |
| Polymerization degree "n" | 0.1168 | 1.0000 |
| Polymerization degree "n + 1" | 0.1088 | 0.9315 |

[The polymerization degree "n" of a polyglycerol showing the highest distribution rate (mode) was 8]

Example 3

Figure 3:
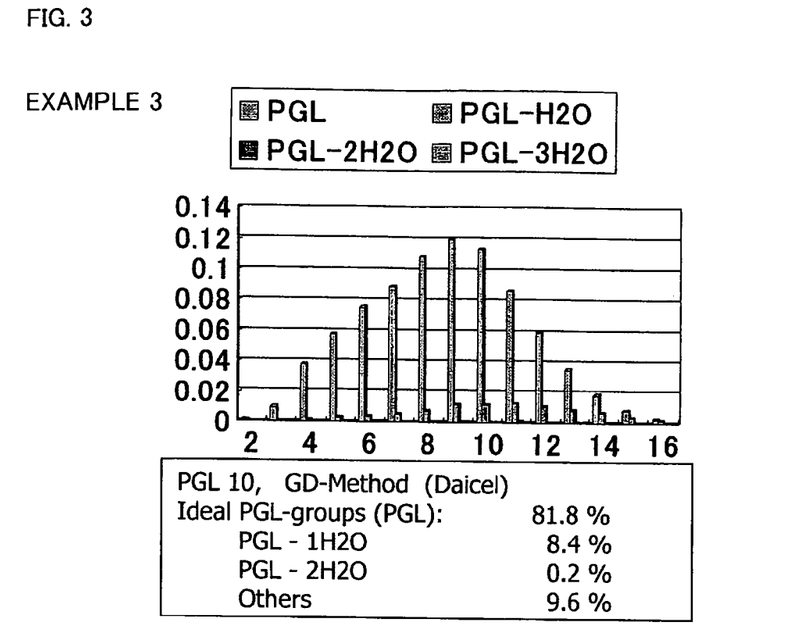
FIG. 3 is a chart showing a composition distribution of a reaction product according to Example 3.

Into the same flask as that used in Example 2, 2.0 mole (188 g) of glycerol was added, and the glycerol was heated to 100° C. Subsequently, while a reaction temperature was maintained at 100° C., 18.0 mole (1,332 g) of glycidol and 1.525 g of phosphoric acid (a product of 85%) were separately dropped therein over 6 hours to continue the reaction until the concentration of oxirane in the system reached less than 0.1%. After cooling, a reaction product was taken out to obtain approximately 1,500 g of a polyglycerol (PGL 10: average polymerization degree of approximately 10). The polyglycerol showed an OH value of 885 mg-KOH/g. FIG. 3 shows the LC/MS analysis results of the obtained polyglycerol. As Table 3 shows, in the reaction product obtained in the polymerization step according to the process of the present invention, components with varying degrees of polymerization except unreacted glycerol provided a preferred distribution as that in Example 1.

Figure 8:
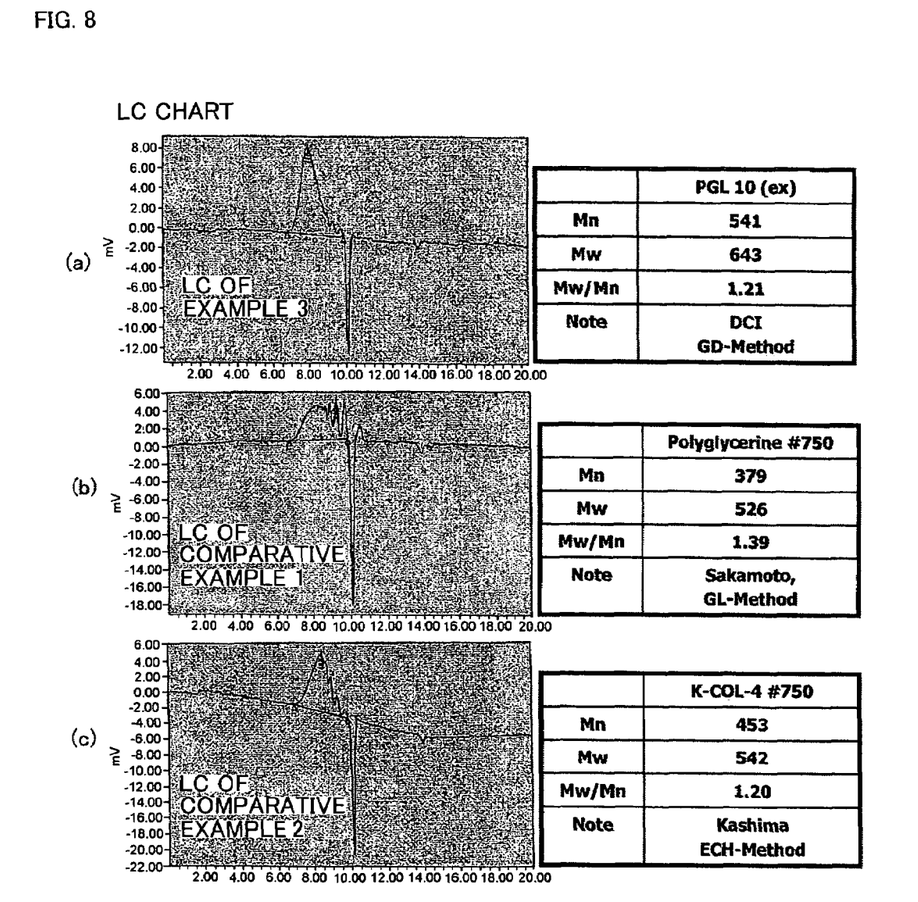

FIG. 8(a) shows a liquid chromatogram of the reaction product of Example 3. In each of the liquid chromatograms shown below, the horizontal axis represents an elution time and the vertical axis represents a peak intensity (unit mV) of the chromatogram.

TABLE 3

Intensity ratio in componential analysis of a polyglycerol in Example 3

| | Intensity ratio in componential analysis | Ratio with respect to mode |
|---|---|---|
| Polymerization degree "n − 1" | 0.1083 | 0.9077 |
| Polymerization degree "n" | 0.1193 | 1.0000 |
| Polymerization degree "n + 1" | 0.1127 | 0.9446 |

[The polymerization degree "n" of a polyglycerol showing the highest distribution rate (mode) was 8]

Example 4

Figure 4:
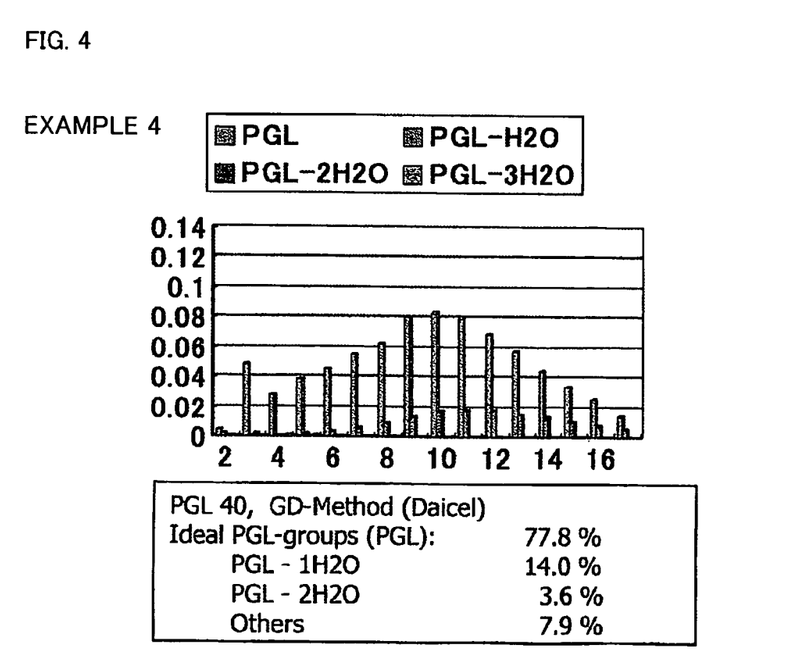
FIG. 4 is a chart showing a composition distribution of a reaction product according to Example 4.

Into the same flask as that used in Example 2, 0.5 mole (47 g) of glycerol was added, and the glycerol was heated to 120° C. Subsequently, while a reaction temperature was maintained at 120° C., 19.5 mole (1,443 g) of glycidol and 1.525 g of phosphoric acid (a product of 85%) were separately dropped therein over 12 hours to continue the reaction until the concentration of oxirane in the system reached less than 0.1%. After cooling, a reaction product was taken out to obtain approximately 1,500 g of a polyglycerol (PGL 40: average polymerization degree of approximately 40). The polyglycerol showed an OH value of 787 mg-KOH/g. FIG. 4 shows the LC/MS analysis results of the obtained polyglycerol. As Table 4 shows, in the reaction product obtained in the polymerization step according to the process of the present invention, components with varying degrees of polymerization except unreacted glycerol provided a preferred distribution as that in Example 1.

TABLE 4

Intensity ratio in componential analysis of a polyglycerol in Example 4.

| | Intensity ratio in componential analysis | Ratio with respect to mode |
|---|---|---|
| Polymerization degree "n − 1" | 0.0799 | 0.9626 |
| Polymerization degree "n" | 0.0830 | 1.0000 |
| Polymerization degree "n + 1" | 0.0793 | 0.9614 |

[The polymerization degree "n" of a polyglycerol showing the highest distribution rate (mode) was 8]

Comparative Example 1

Figure 5:
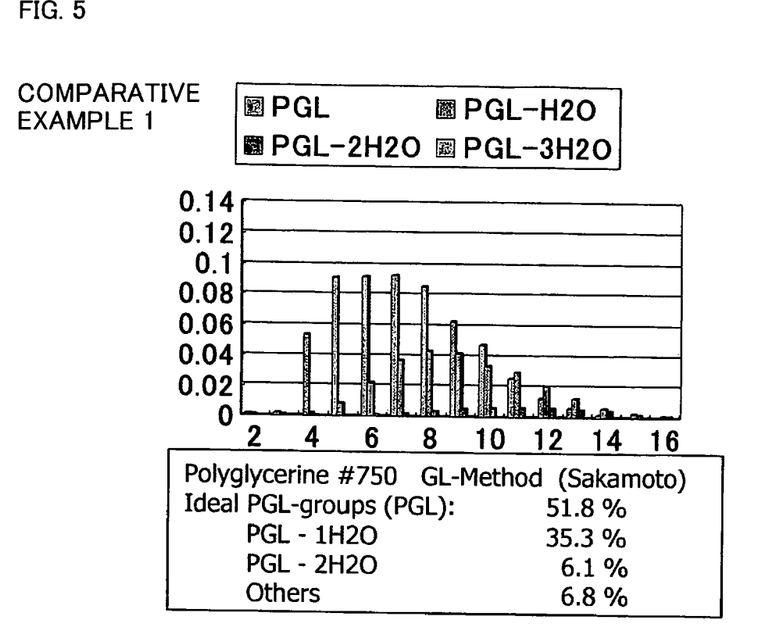
FIG. 5 is a chart showing a composition distribution of a reaction product according to Comparative Example 1.

Commercially available decaglycerol (available from Sakamoto Yakuhin Co., Ltd., Decaglycerol #750; a polyglycerol obtained through dehydration condensation of glycerol, OH value of 890 mg-KOH/g) was analyzed by the above LC/MS. FIG. 5 shows the results of componential analysis. The decaglycerol contains a polyglycerol (2) having a cyclic structure in very high content.

Comparative Example 2

Figure 6:
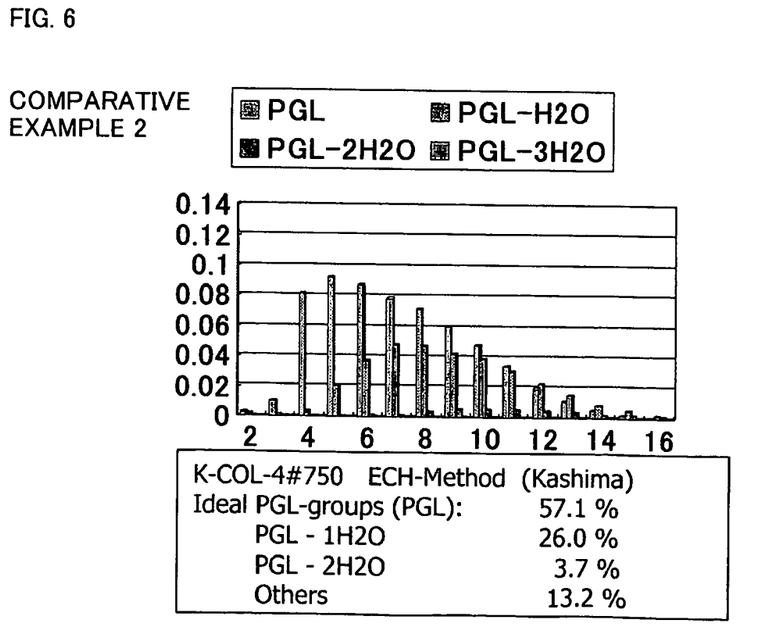
FIG. 6 is a chart showing a composition distribution of a reaction product according to Comparative Example 2.

Commercially available decaglycerol (available from Kashima Chemical Co., Ltd., KCOL-IV-750; a polyglycerol obtained from epichlorohydrin, OH value of 882 mg-KOH/g) was analyzed by the above LC/MS. FIG. 6 shows the results of componential analysis. The decaglycerol contains a polyglycerol (2) having a cyclic structure in high content.

Comparative Example 3

Figure 7:
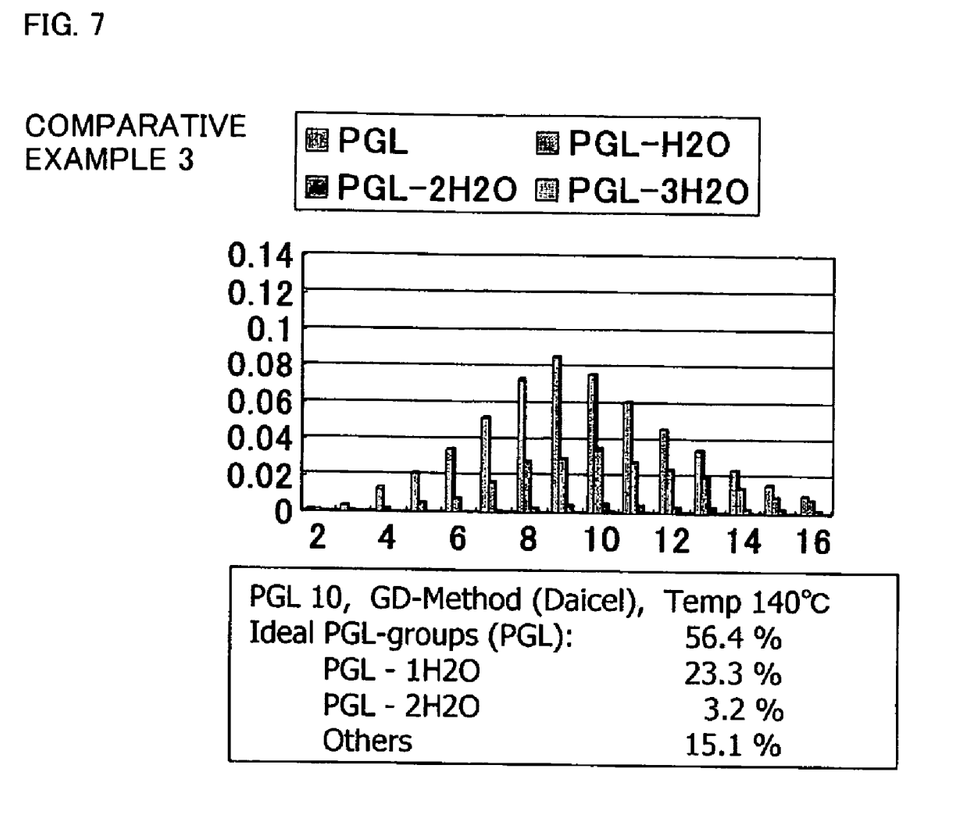
FIG. 7 is a chart showing a composition distribution of a reaction product according to Comparative Example 3.

Into the same flask as that used in Example 2, 2.0 mole (188 g) of glycerol was added, and the glycerol was heated to 140° C. Subsequently, while a reaction temperature was maintained at 140° C., 18.0 mole (1,332 g) of glycidol and 1.525 g of phosphoric acid (a product of 85%) were separately dropped therein over 6 hours to continue the reaction until the concentration of oxirane in the system reached less than 0.1%. After cooling, a reaction product was taken out to obtain approximately 1,500 g of a polyglycerol (PGL 10 of Comparative Example 3: average polymerization degree of approximately 10). The polyglycerol showed an OH value of 887 mg-KOH/g. FIG. 7 shows the LC/MS analysis results of the obtained polyglycerol. The polyglycerol contains a polyglycerol (2) having a cyclic structure and other compounds in high content.

Comparative Example 4

Figure 9:
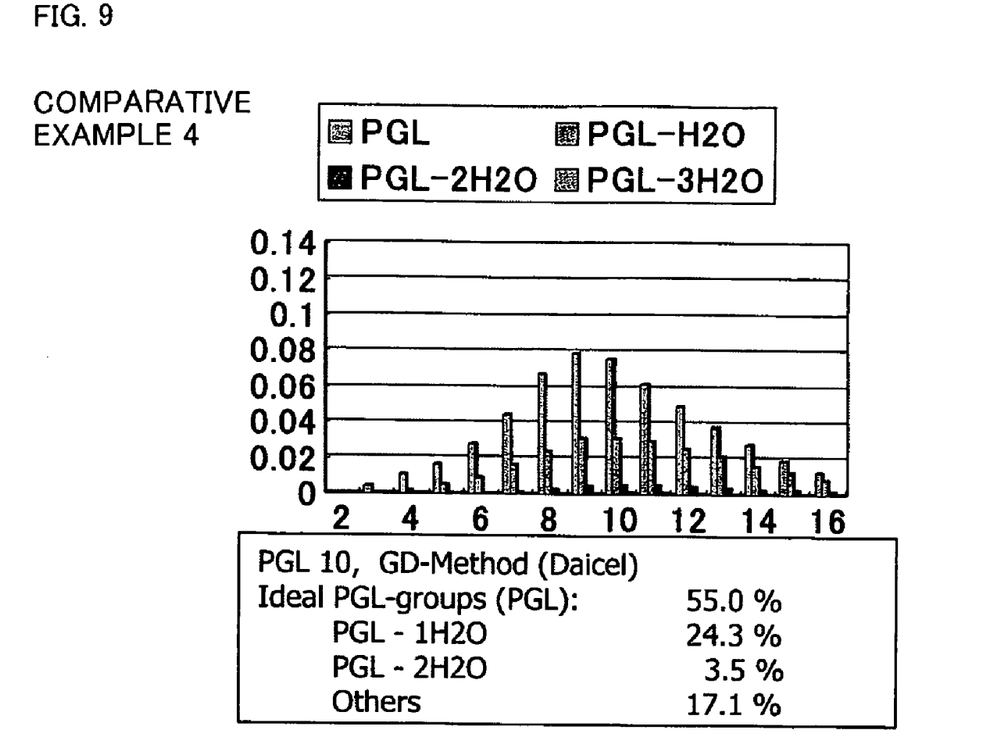
FIG. 9 is a chart showing a composition distribution of a reaction product according to Comparative Example 4.

A reaction was carried out in the same manner as in Example 3 except that 18.0 mole (1,332 g) of glycidol was added dropwise over 6 hours into a flask charged with 2.0 mole (188 g) of glycerol and 1.525 g of phosphoric acid (a product of 85%). The resulting polyglycerol showed an OH value of 885 mg-KOH/g. Approximately 1,500 g of a polyglycerol (PGL 10 of Comparative Example 4: average polymerization of approximately 10) was obtained. FIG. 9 shows the LC/MS analysis results of the obtained polyglycerol. The polyglycerol contains a polyglycerol (2) having a cyclic structure and other compounds in high content.

As described above, glycidol and a catalyst are successively added for a reaction with glycerol, to thereby significantly reduce the amounts of the by-products of a polyglycerol having a cyclic structure. Meanwhile, in the process involving dropping of either glycidol or a catalyst, the amounts of the by-products of a polyglycerol having a cyclic structure are large. Moreover, when a reaction temperature exceeds 130° C., the amounts of the by-products of a polyglycerol having a cyclic structure increase.

Hereinafter, the production of a fatty acid ester of a polyglycerol and its evaluation will be shown.

Example 5

Into a reactor with a volume of 2 liter equipped with a stirrer, a thermometer, a heating jacket, a gas-feed port, and a raw material-feed port, 1,200 g of a polyglycerol obtained in Example 3 (PGL 10: average polymerization degree of approximately 10) was added. Subsequently, lauric acid (99% purity) and a 10% sodium hydroxide aqueous solution were added thereto. The addition amount of lauric acid was adjusted such that a molar ratio of lauric acid/a polyglycerol was 1/1. The amount of sodium hydroxide was 0.0025% by weight with respect to the total amount of a polyglycerol and lauric acid.

After an internal temperature was elevated to 240° C. under normal pressure in a stream of a nitrogen gas for a 3-hour reaction, the internal temperature was further elevated to 260° C. for a reaction for 4 hours. After completion of the reaction, the reactor was cooled to normal temperature to obtain a lauric acid ester of a polyglycerol (PGLE-1).

Comparative Example 5

Esterification was carried out in the same manner as in Example 5 to obtain a lauric acid ester of polyglycerol (PGLE-2), except that the Decaglycerol #750 of Comparative Example 1 was used instead of the polyglycerol (PGL 10:average polymerization degree of approximately 10).

(Evaluation of a Fatty Acid Ester of a Polyglycerol)

PGLE-1 obtained in Example 5 and PGLE-2 obtained in Comparative Example 5 were respectively dissolved in desalted water to prepare 10% aqueous solutions. The states of the solutions stored at 5° C. were observed with time. Table 5 shows the results.

TABLE 5

|  |  | Appearance of 10% aqueous solution | | |
|---|---|---|---|---|
|  | PGLE | Immediately after preparation | One week after preparation | One month after preparation |
| Example 5 | PGLE-1 | Clear | Clear | Clear |
| Comparative Example 5 | PGLE-2 | Slightly cloudy | Precipitation | Precipitation |

INDUSTRIAL APPLICABILITY

A polyglycerol having a cyclic structure in low content according to the present invention has a reduced content of a polyglycerol having a cyclic structure formed through intramolecular dehydration, and thus has a large OH value. As a result, the polyglycerol having a cyclic structure in low content can be used in humectants, thickeners, plasticizers, hydrophilic treatment, and so on. Moreover, a fatty acid ester of a polyglycerol obtained from the polyglycerol and a fatty acid ester has enhanced properties such as emulsification, solubilization, dispersion, washing, anticorrosion, lubrication, static protection, wetting, and can be used as additives for foods and cosmetic, medical, and industrial surfactants. Furthermore, the polyglycerol itself can be used in humectants, thickeners, plasticizers, hydrophilic treatment, and so on.

The invention claimed is:

1. A polyglycerol having a cyclic structure in low content, wherein:
   a ratio of [total polyglycerol (1) represented by the following general formula [1]] to [total polyglycerol (2) having a cyclic structure that contains at least one cyclic structure in a molecule], that is, [the total polyglycerol (1)]: [the total polyglycerol (2) having a cyclic structure] is 70% or more:30% or less (the total of both is 100% by weight) in terms of an intensity ratio determined by liquid chromatography/mass spectrometry; and
   an average calculated from a hydroxyl value of polymerization degree (repeating unit of a glycerol residue) p+2 of polyglycerol (1) and polymerization degree of polyglycerol (2) is 2 or more:

[1]

(in the formula [1], "p" represents a repeating portion of a glycerol residue and is an integer of 0 or more, and a polyglycerol molecule has a polymerization degree of "p+2").

2. A polyglycerol having a cyclic structure in low content according to claim 1, wherein the polyglycerol (2) having a cyclic structure comprises a polyglycerol having a cyclic structure containing a structure represented by the following general formula [2]:

[2]

(in the formula [2], "p" represents a repeating port on of a glycerol residue and is an integer of 0 or more; a structure an "q" represents cyclic portion and is integer of 1 or more; the polyglycerol molecule has a polymerization degree of "p+2q+1"; the cyclic structure portion(s) may be inserted randomly or continuously between the glycerol residues; and the polyglycerol having a cyclic structure in low content, which is a mixture of the polyglycerol molecules, has the average calculated from a hydroxyl value of polymerization degree p+2 of polyglycerol (1) and polymerization degree p+2q+1 of polyglycerol (2) of 2 or more).

3. A polyglycerol having a cyclic structure in low content according to claim 1, wherein the polyglycerol (2) having a cyclic structure comprises a polyglycerol having a cyclic structure containing a structure represented by the following general formula [3]:

[3]

(in the formula [3], "p" represents a repeating portion of a glycerol residue and is an integer of 0 or more; and the polyglycerol molecule has a polymerization degree of "p+3").

4. A polyglycerol having a cyclic structure in low content according to claim 1, wherein the average calculated from a hydroxyl value of polymerization degree p+2 of polyglycerol (1) and polymerization degree of polyglycerol (2) is 3 to 60.

5. A polyglycerol having a cyclic structure in low content according to claim 1, wherein a ratio of [the total polyglycerol (1]:[the total polyglycerol (2) having a cyclic structure] is [80% or more]:[20% or less] (the total of both is 100% by weight): and the average calculated from a hydroxyl value of polymerization degree p+2 of polyglycerol (1) and polymerization degree of polyglycerol (2) is 2 to 10.

6. A polyglycerol having a cyclic structure in low content according to claim 1, wherein a ratio of [the total polyglycerol (1)]:[the total polyglycerol (2) having a cyclic structure] is [70% or more]:[30% or less] (the total of both is 100% by weight); and the average calculated from a hydroxyl value of polymerization degree p+2 of polyglycerol (1) and polymerization degree of polyglycerol (2) is greater than 10.

7. A polyglycerol having a cyclic structure in low content according to claim 1, wherein a ratio of a component with a polymerization degree p+1 to a polyglycerol showing the highest distribution rate (with a polymerization degree p+2) in terms of an intensity ratio distribution determined by liquid chromatography/mass spectrometry, that is, (component with a polymerization degree p+1)/(component with a polymerization degree p+2) is 0.4 or more.

8. A polyglycerol having a cyclic structure in low content obtained through the process for producing a polyglycerol having a cyclic structure in low content according to claim 1, wherein a fluctuation trend of ratio of (component with a polymerization degree p+1)/(component with a polymerization degree p+2) and of (component with a polymerization degree p+3)/(component with a polymerization degree p+2) in terms of intensity ratio determined by liquid chromatography/mass spectrometry corresponds to a distribution obtained through a successive reaction of glycidol using glycerol as an initiator.

9. A polyglycerol having a cyclic structure in low content obtained through the process for producing a polyglycerol having a cyclic structure in low content according to claim 1, wherein a fluctuation trend of ratio of (component with a polymerization degree p+1)/(component with a polymerization degree p+2) and of (component with a polymerization degree p+3)/(component with a polymerization degree p+2) in terms of intensity ratio determined by liquid chromatography/mass spectrometry corresponds to a distribution obtained through a successive reaction of glycidol using glycerol as an initiator.

10. A fatty acid ester of a polyglycerol having a cyclic structure in low content, comprising an ester structure formed through a dehydration reaction of a polyglycerol having a cyclic structure in low content according to claim 1 with a fatty acid having 2 to 30 carbons.

11. A fatty acid ester of a polyglycerol having a cyclic structure in low content, comprising an ester structure formed through a dehydration reaction of a polyglycerol having a cyclic structure in low content according to claim 7 with a fatty acid having 2 to 30 carbons.

12. A Patty acid ester of a polyglycerol having a cyclic structure in low content, comprising an ester structure formed through a dehydration reaction of a polyglycerol having a cyclic structure in low content according to claim 8 with a fatty acid having 2 to 30 carbons.

13. A fatty acid ester of a polyglycerol having a cyclic structure in low content, comprising an ester structure formed through a dehydration reaction ola polyglycerol having a cyclic structure in low content according to claim 9 with a fatty acid having 2 to 30 carbons.

* * * * *